US009500596B2

(12) United States Patent
Gosteli et al.

(10) Patent No.: US 9,500,596 B2
(45) Date of Patent: Nov. 22, 2016

(54) SENSOR AND METHOD OF SENSING

(75) Inventors: Julien Gosteli, Echallens (CH); Fabien Ravet, Pully (CH); Etienne Rochat, Valeyres-sous-Ursins (CH)

(73) Assignee: OMNISENS SA, Morges (CH)

( * ) Notice: Subject to any disclaimer, the term of this patent is extended or adjusted under 35 U.S.C. 154(b) by 317 days.

(21) Appl. No.: 14/233,168

(22) PCT Filed: Jul. 27, 2011

(86) PCT No.: PCT/EP2011/062887
§ 371 (c)(1),
(2), (4) Date: Jan. 16, 2014

(87) PCT Pub. No.: WO2013/013712
PCT Pub. Date: Jan. 31, 2013

(65) Prior Publication Data
US 2014/0152982 A1    Jun. 5, 2014

(51) Int. Cl.
*G01M 11/00* (2006.01)
*G01N 21/88* (2006.01)
*G01M 11/08* (2006.01)
*G01D 5/353* (2006.01)
*G01L 1/24* (2006.01)

(52) U.S. Cl.
CPC ...... *G01N 21/8806* (2013.01); *G01D 5/35364* (2013.01); *G01L 1/242* (2013.01); *G01M 11/085* (2013.01); *G01M 11/319* (2013.01); *G01M 11/39* (2013.01)

(58) Field of Classification Search
None
See application file for complete search history.

(56) References Cited

U.S. PATENT DOCUMENTS

| 5,452,124 A | 9/1995 | Baker |
| 5,812,306 A | 9/1998 | Mizrahi |
| 2008/0068586 A1* | 3/2008 | Kishida ............... G01B 11/18 356/32 |

(Continued)

OTHER PUBLICATIONS

Voskoboinik, Asher, et al. "SBS-based fiber optical sensing using frequency-domain simultaneous tone interrogation." Journal of Lightwave Technology 29.11 (2011): 1729-1735.*

(Continued)

*Primary Examiner* — Kara E Geisel
*Assistant Examiner* — Rebecca C Bryant
(74) *Attorney, Agent, or Firm* — Pearne & Gordon LLP

(57) ABSTRACT

According to the invention, these aims are achieved by means of a sensor, suitable for sensing one or more properties of one or more structures, the sensor comprising, a first optical propagation path which is configurable to cooperate with a structure whose properties are to be sensed; a second optical propagation path which is configurable to cooperate with a structure whose properties are to be sensed; a third optical propagation path; a means for amplifying a signal which propagates in the third optical propagation path, so that the signal is amplified before it begins propagation along the second optical propagation path, and a means to prevent the propagation of signals from the second optical propagation path to the third optical propagation path. There is further provided a corresponding method of sensing.

15 Claims, 7 Drawing Sheets

(56) References Cited

U.S. PATENT DOCUMENTS

| | | | |
|---|---|---|---|
| 2010/0128257 A1* | 5/2010 | Yamamoto | C03B 37/02745 356/73.1 |
| 2011/0228255 A1* | 9/2011 | Li | G01B 11/18 356/33 |

OTHER PUBLICATIONS

Yang, Jing, et al. "Suppression of polarization sensitivity in BOTDA fiber distributed sensing system." 19th International Conference on Optical Fibre Sensors. International Society for Optics and Photonics, 2008.*

International Search report for Application No. PCT/EP2011/062887 dated Jun. 11, 2012.

S. Hasegawa; T. Yari; M. Toyama; K. Nagai; Y. Koshioka; "Declamation detection using embedded BOCDA optical fiber sensor" Sensors and smart structures technologies for civil, mechanical and aerospace systems. 2010.

Hotate, Kazuo. "Distributed Dynamic Strain Measurement Using a Correlation-Based Brillouin Sensing System" IEEE Photonics Technology Letters, vol. 15, No. 2 dated Feb. 2003.

Duckey Lee; Hosung Yoon; Pilhan Kim; Jonghan Park; Namkyoo Park; "Optimization of SNR Improvement in the Noncoherent OTDR Based on Simplex Codes" Journal of Lightwave Technology, vol. 24, No. 1, Jan. 2006.

Kwang Yong Song; Miguel Gonzalez Herraez; Luc Thevenaz, "Long optically controlled delays in optical fibers" Optics Letters vol. 30, No. 14 dated Jul. 15, 2005.

Marcelo A. Soto; Gabriele Bolognini; Fabrizio Di Pasquale. "Long-range simplex-coded BOTDA sensor over 120 km distance employing optical preamplification" Optics Letters vol. 36, No. 2 dated Jan. 15, 2011.

M. Yadlowsky, "Bidirectional optical amplifiers for high-performance WDM systems," in Optical Amplifiers and Their Applications, M. Zervas, A. Willner, and S. Sasaki, eds., vol. 16 of OSA Trends in Optics and Photonics Series (Optical Society of America, 1997), paper SN2.

Sonia Martin-Lopez; Mercedes Alcon-Camas; Felix Rodriguez; Pedro Corredera; Juan Diego Ania-Castanon; Luc Thevenaz; Miquel Gonzalez-Herraez; "Brillouin optical time-domain analysis assisted by second-order Raman amplification" Optics Express, vol. 18, No. 18, dated Aug. 30, 2010.

Vedadi et al. "Brillouin Optical Time-Domain Analysis of Fiber-Optic Parametric Amplifiers" IEEE Photonics Technolgy Letters, vol. 19, No. 3, Feb. 1, 2007.

Stella Foaleng Mafang, "Brillouin Echoes for Advanced Distributed Sensing in Optical Fibres" École Polytechnique Fédérale De Lausanne, doctoral thesis presented Mar. 11, 2011.

Martin-Lopez et al., "Brillouin optical time-domain analysis assisted by second-order Raman amplification" Optic Express, Aug. 30, 2010 , vol. 18, No. 18.

Govind P. Agrawal, "Nonlinear Fiber Optics", Academic Press, University of Rochester, 2001.

* cited by examiner

SENSOR AND METHOD OF SENSING

FIELD OF THE INVENTION

The present invention concerns a sensor and method of sensing, and particular, but not exclusively to a sensor and method of sensing which measures properties of one or more structures using Brillouin scattering techniques.

DESCRIPTION OF RELATED ART

In many fields of application, like pipeline, power cables or subsea, the use of measuring apparatuses to monitor continuously structural and/or functional parameters is well known. The measuring apparatuses can be applied also to the civil engineering sector, and in particular in the field of the construction of structures of great dimensions.

The measuring apparatuses are commonly used to control the trend over time of the temperature or of the strain, i.e. of the geometrical measure of the deformation or elongation resulting from stresses and defining the amount of stretch or compression along the fibre, of the respective structure. In more detail, these measuring apparatuses are suitable to give information of local nature, and they can be therefore used to monitor, as a function of the time, the temperature or the strain associated with a plurality of portions and/or of components of the engineering structure to be monitored, providing useful information on leak, ground movement, deformation, etc. of the structure.

Among the measuring apparatuses used to monitor the status of engineered or architectonic structures, the optoelectronic devices based upon optical fibres have a great significance. In particular, these apparatuses normally comprise an electronic measuring device, provided with an optical fibre probe which is usually in the order of a few tens of kilometers. In use, this optical fibre is coupled stably to, and maintained substantially into contact with, portions or components of the engineered structure, whose respective physical parameters shall be monitored. For example, this optical fibre can run along the pipes of an oil pipeline, or it can be immersed in a concrete pillar of a building, so that it can be used to display the local trend of the temperature or of the strain of these structures. In other words these optoelectronic devices comprise fibre optical sensors, i.e. sensors using the optical fibre as the sensing element. Fibre optical sensors can be:

- point sensors, wherein only one location along the optical fibre is made sensitive to the temperature and/or the strain;
- quasi-distributed sensors or multiplexed sensors, wherein many point sensors are connected to each other by an optical fibre and multiplexed along the length of the fibre by using different wavelength of light for each sensor; or
- distributed or fully distributed sensors, wherein the optical fibre is a long uninterrupted linear sensor.

These measuring instruments based upon optical fibres can be subdivided into various types depending upon both the physical quantity/ies they are suitable to measure and the physical principle used to detect this quantity/these quantities.

When a powerful light pulse of wavelength $\lambda_0$ (or frequency $v_0 = c/\lambda_0$, wherein c is the speed of light), known as the pump, propagates through an optical fibre, a small amount of the incident power is scattered in every directions due to local non-homogeneities within the optical fibre. If the optical fibre is a single-mode fibre (SMF), i.e. a fibre designed for carrying a single ray of light (mode) only, then only forward and backward scattering are relevant since the scattered light in other directions is not guided. Backscattering is of particular interest since it propagates back to the fibre end where the laser light was originally launched into the optical fibre.

Scattering processes originate from material impurities (Raleigh scattering), thermally excited acoustic waves (Brillouin scattering) or atomic or molecular vibrations (Raman scattering).

Distributing sensing techniques relay on the analysis of the backscattered signal created at different location along the fibre.

RAYLEIGH SCATTERING is the interaction of a light pulse with material impurities. It is the largest of the three backscattered signals in silica fibres and has the same wavelength as the incident light. Rayleigh scattering is the physical principle behind Optical Time Domain Reflectometer (OTDR).

BRILLOUIN SCATTERING is the interaction of a light pulse with thermally excited acoustic waves (also called acoustic phonons). Acoustic waves, through the elasto-optic effect, slightly, locally and periodically modify the index of refraction. The corresponding moving grating reflects back a small amount of the incident light and shifts its frequency (or wavelength) due to the Doppler Effect. The shift depends on the acoustic velocity in the fibre while its sign depends on the propagation direction of the travelling acoustic waves. Thus, Brillouin backscattering is created at two different frequencies around the incident light, called the Stokes and the Anti-Stokes components. In silica fibres, the Brillouin frequency shift is in the 10 GHz range (0.1 nm in the 1550 nm wavelength range) and is temperature and strain dependent.

RAMAN SCATTERING is the interaction of a light pulse with thermally excited atomic or molecular vibrations (optical phonons) and is the smallest of the three backscattered signals in intensity. Raman scattering exhibits a large frequency shift of typically 13 THz in silica fibres, corresponding to 100 nm at a wavelength of 1550 nm. The Raman Anti-Stokes component intensity is temperature dependent whereas the Stokes component is nearly temperature insensitive.

FIG. 1 schematically shows a spectrum of the backscattered light generated at every point along the optical fibre when a laser light is launched in the optical fibre. The higher peak, at the wavelength $\lambda_0$, corresponding to the wavelength of a single mode laser, is the Rayleigh peak, originated from material impurities. The so-called Stokes components and the so-called anti-Stokes components are the peaks at the right side respectively left side of the Rayleigh peak. The anti-Stokes Raman peak, originated from atomic or molecular vibrations, has an amplitude depending on the temperature T. The Stokes and anti-Stokes Brillouin peaks, generated from thermally excited acoustic waves, have a frequency depending on the temperature T and on the strain $\epsilon$.

The Brillouin shift (wavelength position with respect to the original laser light) is an intrinsic physical property of the fibre material and provides important information about the strain and temperature distribution experienced by an optical fibre.

The frequency information of Brillouin backscattered light can be exploited to measure the local temperature or strain information along an optical fibre. Standard or special single-mode telecommunication fibres and cables can be used as sensing elements. The technique of measuring the local temperature or strain is referred to as a frequency-based technique since the temperature or strain information is contained in the Brillouin frequency shift. It is inherently more reliable and more stable than any intensity-based technique, such as the Raman effect, which are sensitive to drifts, losses and variations of attenuations. As a result, the Brillouin based technique offers long term stability and large immunity to attenuation. In addition, the Brillouin scattering must satisfy a very strict phase condition, making the interaction to manifest as a spectrally narrow resonance, resulting in an accurate measurement. This process of propagating a pulse of light into the optical fibre and measuring the backscattering signal is called Spontaneous Brillouin Scattering (SPBS): it is a weak processing which leads to a low intensity scattered light.

The Brillouin scattering process has the particularity that it can be stimulated by a second optical signal—called the probe—in addition to the first optical signal—called the pump—that generated the scattering, providing that the probe fulfils specific conditions. This property is especially interesting for sensing applications and can be achieved by the use of a probe counter propagating with respect to the pump. Stimulation is maximized when pump and probe frequencies (or wavelengths) are exactly separated by the Brillouin shift. In this case, the energy transferred from the pump to the probe (or vice and versa depending on the selected Stokes/antistokes backscattering signal) results in a greatly enhanced backscattered intensity and thus a larger Signal-to-Noise Ratio (SNR). This is seen as a resonant phenomenon where an amplification of the probe power occurs at the expense of the pump when the resonant condition is fulfilled, i.e. when the frequency difference between pump and probe matches the local Brillouin frequency.

In the known solutions the pump is composed by one or more nanoseconds long optical pulses and the probe by a Continuous Wave—CW light, as it will be discussed.

Optoelectronic measurement devices based on Stimulated Brillouin Backscattering (SBS) are known as Brillouin Optical Time Domain Analysers or BOTDA; as opposed to Brillouin Optical Time Domain Reflectometers (BOTDR) which are based on spontaneous Brillouin backscattering (SPBS).

An optoelectronic measurement device based on BOTDA normally performs a frequency domain analysis and a time domain analysis.

Frequency domain analysis: the temperature/strain information is coded in the Brillouin frequency shift. Scanning the probe frequency with respect to the pump while monitoring the intensity of the backscattered signal allows to find the Brillouin gain peak, and thus the corresponding Brillouin shift, from which the temperature or the strain can be computed. This is achieved by using two optical sources, e.g. lasers, or a single optical source from which both the pump signal and the probe signal are created. In this case, an optical modulator (typically a telecommunication component) is used to scan the probe frequency in a controlled manner.

Time domain analysis: due to the pulsed nature of the pump, the pump/probe interaction takes place at different location along the fibre at different times. For any given location, the portion of probe signal which interacted with the pump arrives on a detector after a time delay equal to twice the travelling time from the fibre input to the specified location.

Thus, monitoring the backscattered intensity with respect to time, while knowing the speed of light in the fibre, provides information on the position where the scattering took place.

Typical commercial optoelectronic measurement devices based on BOTDA can measure temperature/strain over 30 km of fibre with a spatial resolution of 1 m (equivalent to 30,000 distinct independent sensors). The resolution on temperature is typically <1 K and is typically 20µε for strain.

Any stimulated Brillouin scattering-based sensing system suffers from two fundamental limitations, which restrict the maximal sensing range and the measurement accuracy.

The first limitation is the inevitable fiber intrinsic loss, showing a typical value of 0.2 dB/km in a standard single mode fiber at a wavelength of 1550 nm. Thus, the optical waves for the sensing undergo a non-negligible power attenuation while propagating through sensing fibers. The intensity of the Brillouin pump $I_P$ is expressed as:

$$I_P(z) = I_{Po} e^{-\alpha z}.$$

Where $I_{po}$ is the pump power at the entrane of a fibre, a is the fibre attenuation and z is the position along the fibre. Consequently, Brillouin gain $G=e^G$ represents the net signal power gain experienced through the SBS interaction—decreases with respect to the position along the sensing fiber:

$$G = g_B L_{eff} I_{Po} e^{-\alpha z}.$$

where $g_B$ is the peak value of Brillouin gain, $L_{eff}$ is the effective fiber length. It is clearly seen that the contrast of the detected signal degrades in distance due to the pump power attenuation.

The incident pump power can be increased as a solution to compensate the fiber loss. However, the associated non-linear phenomena such as modulation instability and Raman amplification due to the high intensity will deplete the pump itself and limit the maximal input pump power. Practically, this limits the range over which sensing can take place to about 30 km to 50 km.

The second limitation results from the depletion of the pump signal in large gain regime, that is a non-linear transfer of the pump power to the probe power taking place over a short distance and biasing the measurement. To achieve a high quality signal in terms of the signal-to-noise ratio (SNR), hence a longer measurement range, a high signal power would be required in the sensing system. However, it turns out that this configuration leads to a pump depletion that will make the sensing system nonlinear, and therefore not suitable for certain applications.

Previously, three techniques have been demonstrated as robust solutions to improve the sensing measurement range and the measurement accuracy.

Firstly, two distinct Brillouin scattering-based optical reflectometers can be installed from one monitoring station to a remote destination and from another monitoring station to the same destination, hence increasing the measurement range by a factor of two thanks to the one-end access feature of this type of sensing system. This also increase cost by a factor two. Similarly, when the sensing distance mid-point is accessible, one instrument can be used to measure half the distance in each direction; however, it increases measurement time by a factor two.

Secondly, coding technique was implemented in typical Brillouin sensing systems. A key advantage of coding technique relies on a high signal gain without pump depletion, so as to improve to a large increment the signal-to-noise ratio. With standard fibre loss, this already corresponds to measure temperature/strain over 50 km of fibre. This demonstration was based on a coding called SIMPLEX, commonly used in other domains in engineering. The implementation of such a coding requires no modification of the hardware of the device, just a change in the software driving the device and a substantial overhead in calculations, so that it can be seen like an upgrade at a very low added cost. However, SIMPLEX code is efficient if it is composed by "return to zero" (RZ) signals, which are more difficult to manage then "non return to zero" (NRZ) signals which limits its practicality.

Lastly, Raman amplification was used to entirely compensate the fiber intrinsic loss, so as to make the sensing fiber fully transparent for the signal waves. However, the spontaneous noise generated from Raman amplifiers may impair the sensing system.

Despite these technical difficulties, it is important to offer an optoelectronic measurement device with a 100 km range and a metric spatial resolution.

The intrinsic fiber loss is currently regarded as an inevitable bottleneck in any optical telecommunication link. When the link length to transfer information from one point to another point exceeds a certain value, typically >80 km, the signal power becomes too small to be reliably detected. This causes a significant increase of beat-error-ratio (BER), hence a degradation of the signal fidelity.

The corresponding effect, for instance in Brillouin based sensing application, is a gradual exponential decrease of the power of the pump signal whilst it propagates through a sensing fiber; this results in a decrease of the back-scattered signal amplitude, so that the back-scattered signal becomes too weak to deliver reliable information.

In optical communication systems, optical amplifiers are commonly used for the fiber loss compensation, as shown in FIG. 2.

FIG. 2 shows a known optical communication link 1 between a transmitter 2 and receiver 4, with period implementation of optical amplifiers 3 which amplify signals which propagate in the optical communication link 1, to compensate for fiber loss. However, for Brillouin sensing/sensors, a modification of amplification systems is required, since the installed amplifier must amplify only a pump signal (in the figure travelling from left to right), and not a probe signal (in the figure travelling from right to left) which is used to stimulate Brillouin backscattering. Otherwise, the amplified probe will lead to depletion of the pump signal, and result in non-linear behaviour of the pump signal.

FIG. 3 depicts the schematic diagram of the Brillouin pump repeater 5. The Brillouin pump repeater 5 basically consists of an optical amplifier 7 and two optical circulators 9. A simple optical circulation circuit 11 can be made of two optical circulators. The role of the optical circuit 11 is to allow only a Brillouin pump signal to be amplified by the amplifier 7, while ensuring a probe signal is transmitted in the other direction through the Brillouin pump repeater 5 without being amplified. In other word, the Brillouin pump repeater acts as an optical amplifier for the pump signal, but it is fully transparent for the probe signal. Moreover, an optical filter must be placed after the amplifier to completely suppress the amplified spontaneous noise generated from the amplifier (not shown).

Brillouin pump repeaters can be used to compensate for the gradual exponential decrease of the power of the Brillouin pump as it propagates through the sensing fiber, but Brillouin pump repeaters are not sufficient to enable sensing over long distances.

In stimulated Brillouin scattering-based sensors, the probe signal also generates backward-propagating spontaneous Brillouin Stokes and anti-Stokes waves, hence co-propagating with the pump signal in the fiber. These two waves are spectrally so close to the pump signal that it is practically impossible to filter them out using a commercial optical filter. Thus, the probe generated spontaneous Brillouin Stokes and anti-Stokes waves are amplified along with the pump signal by the Brillouin pump repeater. The amplified spontaneous Brillouin Stokes and anti-Stokes waves can act as detrimental noise sources for the sensing system section located after the amplifier. In fact, the amplified spontaneous Brillouin Stokes and anti-Stokes waves lead to critical impairments of the function of the sensor system, by raising nonlinear parametric processes such as additional stimulated Brillouin interactions and four wave mixing process.

It is an aim of the present invention to obviate, or mitigate, at least some of the afore-mentioned disadvantages.

BRIEF SUMMARY OF THE INVENTION

According to the invention, these aims are achieved by means of a sensor, suitable for sensing one or more properties of one or more structures, the sensor comprising, a first optical propagation path which is configurable to cooperate with a structure whose properties are to be sensed; a second optical propagation path which is configurable to cooperate with a structure whose properties are to be sensed; a third optical propagation path; a means for amplifying a signal which propagates in the third optical propagation path, so that the signal is amplified before it begins propagation along the second optical propagation path, and a means to prevent the propagation of signals from the second optical propagation path to the third optical propagation path.

Advantageously, a pump signal which propagates in the optical propagation path can be amplified by the means for amplifying, before the pump signal begins propagation along the second optical propagation path; this amplification will compensate for losses which have occurred in the pump signal as the pump signal propagated along the third optical propagation path. Thus, the pump signal will have greater power as it begins to propagate along the second optical propagation path. As the pump signal has greater power before it begins to propagate along the second optical propagation path, the backscattered signal which results due to Brillouin scattering, has a greater power. Thus, more accurate sensing of properties of a structure which is in cooperation with an optical fiber which defines the second optical propagation path, can be achieved. Furthermore, the properties of a structure can be sensed over a greater length of structure.

The means to prevent the propagation of signals from the second optical propagation path to the third optical propagation path ensures that a probe signal which propagates along the second optical propagation path is prevented from propagating to the third propagation path. As the probe signal is blocked from propagating along the third propagation path, no spontaneous Brillouin Stokes and anti-Stokes waves which probe signals create, are generated in the third propagation path. Thus, a pump signal which propagates in the third propagation path is not affected by noise created by spontaneous Brillouin Stokes and anti-Stokes waves.

Thus, a pump signal which propagates in the third optical propagation path is spectrally pure (i.e. without stokes/anti-stokes components generated by counter propagating probe). This spectrally pure signal can be amplified and may be provided to the second optical propagation path as a pump signal for the second optical propagation path, enabling more accurate sensing of properties of the one or more structures.

The sensor may further comprise a means to prevent the propagation of signals from the first optical propagation path to the second optical propagation path. This means may be further configured to allow the propagation of signals, from the second optical propagation path to the first optical propagation path and from the third optical propagation path to the second optical propagation path.

The means to prevent the propagation of signals from the first optical propagation path to the second optical propagation path ensures that noise generated by signals in the first optical propagation path is prevented from propagating to second optical propagation path. Furthermore, the means may be configured to prevent the signals which propagate in the first optical propagation path from being amplified by the means for amplifying; thus Brillouin Stokes and anti-Stokes waves which probe signals created in the first optical propagation path will not be amplified, and as discussed previously will not propagate to the second optical propagation path. Thus, the, amplified, spectrally pure, pump signal, which propagates along the second optical propagation path, is unaffected by noise generated in the first optical propagation path.

The means to prevent the propagation of signals of the second optical propagation path to the third optical propagation path, may comprise a circulator circuit. The means to prevent the propagation of signals from the first optical propagation path to the second optical propagation path, may comprise a circulator circuit. The means to prevent the propagation of signals from the first optical propagation path to the second optical propagation path, but to allow the propagation of signals, from the second optical propagation path to the first optical propagation path and from the third optical propagation path to the second optical propagation path, may comprise a circulator circuit.

The sensor may further comprise a circulator circuit which is configured such that it is operable to ensure that only pump signals are amplified by the means for amplifying. The circulator circuit may be further configured such that it is operable to prevent probe signals from being amplified by the means for amplifying. The circulator circuit may be configured to direct a pump signal which has propagated along the third optical propagation path, to the means for amplifying. The circulator circuit may be configured to prevent a probe signal which has propagated along the second optical propagation path, from propagating to the means for amplifying. The circulator circuit may be configured to prevent signals which propagate in the first optical propagation path, from propagating to the means for amplifying.

The amplifying means may be arranged to amplify a pump signal before the pump signal reaches the circulator circuit.

The amplifying means may be configured to amplify signals which propagate in a first direction and to stop signals which propagate in a second direction. Thus, the amplifying means may be a single directional system. This will ensure that even if a first pump signal which propagates in the first optical propagation path would propagate towards the amplifying means the first pump signal would not be amplified, as the first pump signal propagates in the second direction; but a second pump signal which propagates in the third optical propagation path will be amplified by the amplifying means as it propagates in the first direction.

The third optical propagation path may be configurable to be arranged remote to the one or more structures so that a signal propagating in the third optical propagation path is unaffected by properties of the structure.

The sensor may further comprise a means for providing a first pump signal to the first optical propagation path, a means for providing a second pump signal to the third optical propagation path, and a means for providing a probe signal to the second optical propagation path, so that one or more distributed sensing techniques may be carried out to determine properties of the one or more structures. The sensor may further comprise a means for providing a first pump signal to the first optical propagation path, a means for providing a second pump signal to the third optical propagation path, and a means for providing a probe signal to the second optical propagation path, so as to provide stimulated Brillouin scattering which can be used to determine properties of the one or more structures.

The means for providing a first pump signal to the first optical propagation path, means for providing a second pump signal to the third optical propagation path, and means for providing a probe signal to the second optical propagation path, may be integral in the same device.

The means for providing a first pump signal to the first optical propagation path and a second pump signal to the third optical propagation path, and means for providing a probe signal to the second optical propagation path, may comprise at least one of a Brillouin Analyzer, Brillouin Optical Time Domain Analyzer; a Brillouin Optical Frequency Domain Analyzer; a Brillouin Optical Coherence Domain Analyzer.

The means for providing a first pump signal to the first optical propagation path and second pump signal to the third optical propagation path, may comprise a coupling means which is configured to divide a main pump signal to provide a first pump signal and second pump signal.

The first pump signal may be configured to have a higher power than the second pump signal.

The first optical propagation path and the third optical propagation path may be coupled by a coupling means so that a main pump signal can be divided to provide the first pump signal and second pump signal.

The coupling means may comprise a coupler.

The third optical propagation path may be configured such that the time for a signal to propagate along the length of the third optical propagation path is at least equal to the time for a signal to propagate along the length of the first optical propagation path. The third optical propagation path may be configured to have the same properties as the first optical propagation path. The third optical propagation path may be configured to have a length which is at least equal to the length of the first optical propagation path. Preferably, the third optical propagation path is configured to have a length which is greater than the length of the first optical propagation path.

The third optical propagation path may comprise a delay means which is operable to delay a signal which propagates through the third optical propagation path. The delay means may be integral to the third optical propagation path.

The means for amplifying a signal may comprise an optical amplifier.

The means for amplifying a signal may comprise a doped fibre optical amplifier and a means for providing a signal which can cooperate with the doped fibre optical amplifier to configure the doped fibre optical amplifier to provide a predetermined amplification. The means for amplifying could also be a non-fibre based amplifier.

The means for amplifying a signal may comprise an optical parametric amplification pump, which provides an amplification signal which can couple with a pump signal to amplify the pump signal as the pump signal and amplification signal propagate. The optical parametric amplification pump may be configured to generate an optical parametric gain resonance with a programmable spectral bandwidth and net gain value, while a pump signal propagates through the second optical propagation path. A central frequency of the optical parametric amplification pump may be so that a pump signal can be spectrally placed in the centre of an optical parametric amplification gain resonance.

The means for amplifying a signal may comprise a Raman amplifier which provides a Raman signal which can cooperate with a pump signal to amplify the pump signal.

The sensor may comprise a plurality of first optical propagation paths and second optical propagation paths cascaded; a plurality of third optical propagation paths; a plurality of means for amplifying a signal which propagates in the third optical propagation path, so that the signal is amplified before it begins propagation along each of the second optical propagation paths, and a plurality of means to prevent the propagation of signals from each of the second optical propagation paths to each of the third optical propagation paths.

According to the present invention there is further provided a sensor device comprising a plurality of the above-mentioned sensors cascaded.

According to a further aspect of the present invention there is provided a method of sensing properties of one or more structures, using a sensor according to any one of the afore-mentioned sensors, comprising the steps of, arranging the first optical propagation path in cooperation with a structure whose properties are to be sensed;

arranging the second optical propagation path in cooperation with a structure whose properties are to be sensed; and propagating a first pump signal along in the first optical propagation path and propagating a second pump signal along the third optical propagation path;

amplifying the second pump signal only such that the second pump signal is amplified before the second pump signal propagate along the second propagation path;

providing a probe signal which propagates along the first and second optical propagation paths to stimulate Brillouin scattering in both the first pump signal which propagates in the first optical propagation path and in the second pump signal which propagates in the second optical propagation path;

preventing the propagation of the probe signal along the third optical propagation path;

using a backscattered signal which has resulted from the Brillouin scattering, to determine properties of the one or more structures.

The first and second optical propagation path may be arranged in cooperation with the same structure e.g. different parts or portions of the same structure, or with different structures e.g. a first and second structure.

The method may further comprise the step of arranging the third optical propagation path remote to the one or more structures so that a signal propagating in the third optical propagation path is unaffected by properties of the one or more structures.

The method may further comprise the step of blocking the propagation of signals from the first optical propagation path to the second optical propagation path.

The method may further comprise the step delaying the propagation of the second pump signal in the third optical propagation path.

The method may further comprise the step of dividing a main pump signal to provide the first and second pump signal.

The method may further comprise the step of coupling the first and third optical propagation paths so that a main pump signal can be divided to provide the first and second pump signals.

The method may further comprise the step of remotely controlling the amplification of the second pump signal.

The method may further comprise the step of providing a control signal which controls the amplification provided by an amplifier which is operable to amplify a pump signal.

The method may further comprise the step of amplifying the second pump signal as the second pump signal propagates along the third optical propagation path. The method may further comprise the step of providing a gain which amplifies the second pump signal as the second pump signal propagates along the third optical propagation path. The gain may be provided by a signal.

The method may further comprise the step of using a Raman signal to provide a gain which can amplify the second pump signal.

The method may further comprise the step of tuning a central frequency of an optical parametric amplification pump so that the second pump signal is spectrally in the centre of a gain resonance of an amplification signal provided by the optical parametric amplification pump. The amplification signal provided by the optical parametric amplification pump may couple to a pump signal to amplify the pump signal as the amplification signal and pump signal propagate.

The method may further comprise cascading one or more sensors.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
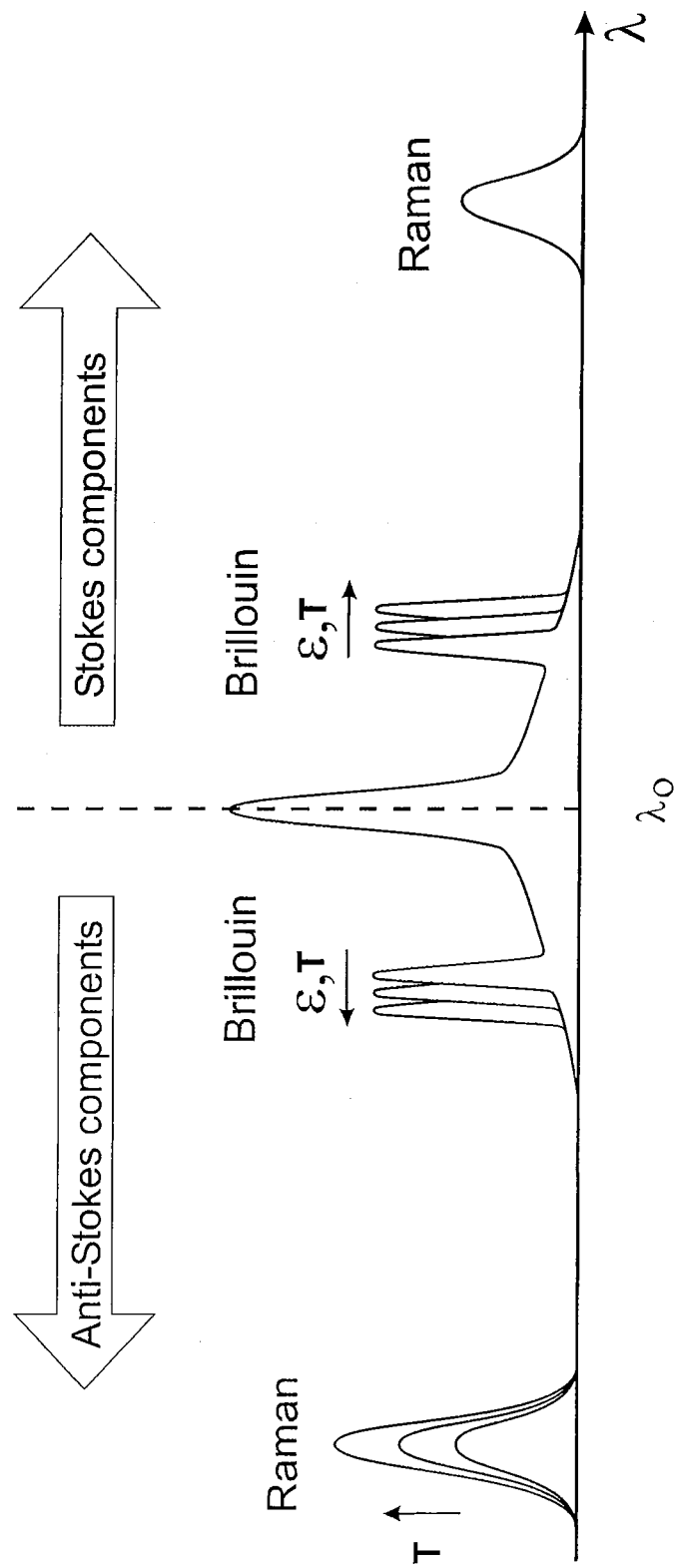
FIG. 1 schematically shows a spectrum of the backscattered light generated at every point along the optical fibre when a laser light is launched in the optical fibre.
Figure 2:
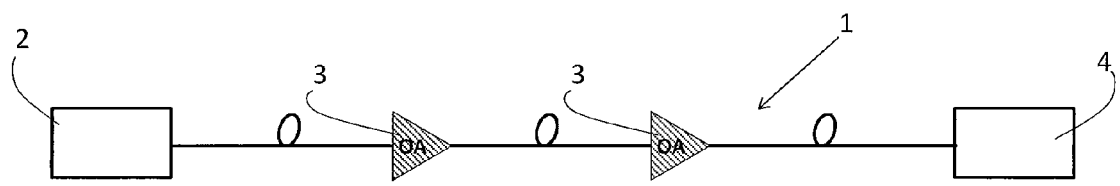
FIG. 2 shows a known optical communication link between a transmitter and receiver, with period implementation of optical amplifiers which compensate for fiber loss.
Figure 3:
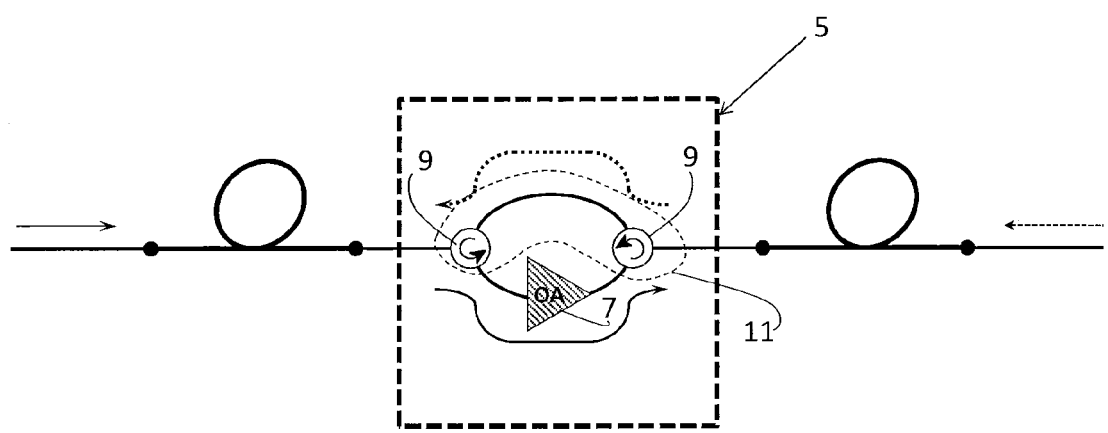
FIG. 3 shows a schematic diagram of the Brillouin pump repeater known in the art.
Figure 4:
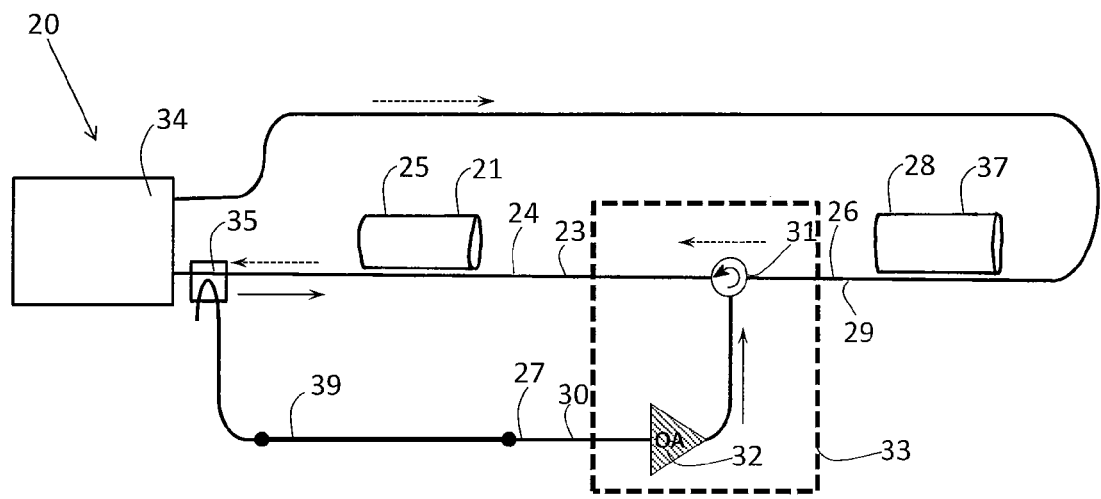
FIG. 4 illustrates a sensor according to one possible embodiment of the present invention.

FIG. 4 illustrates a sensor 20 according to one possible embodiment of the present invention. The sensor 20 is suitable for sensing one or more properties of one or more structures; in the particular example the sensor 20 is used for sensing the temperature and strain of a first and second pipe 21,37.

The sensor 20 comprises a first optical propagation path 23 which is defined by a first optical fiber 24. The first optical fiber 24 is secured to a surface 25 of the first pipe 21 to ensure that changes in the temperature and strain of the first pipe 21 will influence the propagation properties of the first optical fiber 24. A second optical propagation path 26 which is defined by a second optical fiber 29, is further provided. The second optical fiber 26 secured to a surface 28 of the second pipe 37 to ensure that changes in the temperature and strain of the second pipe 37 will influence the propagation properties of the second optical fiber 24.

The sensor 20 further comprises a third optical propagation path 30 which is defined by a third optical fiber 27. The third optical fiber 27 is arranged remotely to both the first and second pipes 21,37.

The third optical fiber 27 is configured such that the time it takes to propagate a signal along the whole length of the third optical propagation path 30 is at least equal to the time it takes for a signal to propagate along the whole length of the first optical propagation path 23. This can be achieved in many different ways; for example by ensuring that the first and third optical fibers 24,27 have the same properties and that the third optical fiber 27 is at least the same length as the first optical fiber 24; alternatively, the third optical fiber 27 may be configured to include a component which can delay propagation in the third optical fiber, for example, an optical delay device or optical delay line. In the particular example shown in FIG. 4 the sensor 20 includes an optical delay line 39, arranged to define part of the third optical propagation path 30. In this particular example the optical delay line is integral to the third optical fiber 27, thus the delay is provided by the fiber itself; however it will be understood that any other delay means could be used. The optical delay line 39 will delay the propagation of signals along the third optical propagation path 30. This, will ensure two distinct information traces obtained from two pipes will not be partially superposed, distorting the acquired information i.e. that a Brillouin back scattered signal generated in the second optical propagation path 26 will not be superposed on a Brillouin back scattered signal generated in the first optical propagation path 23.

The sensor 20 comprises a means, in the form of a circulator circuit 31, to prevent the propagation of signals from the first optical propagation path 23 to the second optical propagation path 26, and from second optical propagation path 26 to the third optical propagation path 30, but to allow the propagation of signals from the second optical propagation path 26 to the first optical propagation path 23, and from the third optical propagation path 30 to the second optical propagation path 26.

A means for amplifying a signal which propagates in the third optical propagation path 30, so that the signal is amplified before it begins propagation along the second optical propagation path 26, is further provided. In this particular example the means for amplifying is an optical amplifier 32 which is located at a junction 33 between the first, second and third optical fibers 24,29,27.

The sensor 20 comprises a coupling means 35 which optically couples the first optical propagation path 23 and the third optical propagation path 30. Any suitable coupling means may be used. Preferably the coupling means 35 may be a 2×2 fibre coupler with a non symmetrical coupling ratio (for instance 95% in the first optical propagation path 23 and 5% in the third optical propagation path 30). The coupling means 35 is configured such that it is operable to divide a main pump signal to provide a first pump signal which can propagate in the first optical propagation path 23 and a second pump signal which can propagate in the third optical propagation path 30.

The sensor further comprises a means for providing a first pump signal to the first optical propagation path 23 and a second pump signal to the third optical propagation path 30, and a means for providing a probe signal to the second optical propagation path 26, so as to provide stimulated Brillouin scattering which can be used to determine properties of a structure. Any suitable means may be used to provide the first and second pump signals and the probe signal. In this particular example a Brillouin Analyzer 34 (one or more of a Brillouin Optical Time Domain Analyzer; Brillouin Optical Frequency Domain Analyzer; Brillouin Optical Coherence Domain Analyzer), provides the probe signal and also provides a main pump signal which is divided to form the first and second pump signals: The Brillouin Analyzer 34 generates a main pump signal, the main pump signal propagates along the first optical propagation path 23 where it is received by the coupling means 35; the coupling means 35 divides the main pump signal to provide a first pump signal which propagates along the first optical propagation path 23 and a second pump signal which propagates along the third optical propagation path 30. Thus, in the example shown in FIG. 4, the means for providing the first and second pump signals comprises the Brillouin Analyzer which provides a main pump signal and coupling means 35 which is configured to divide a received main pump signal to form a first pump signal and a second pump signal.

In this particular example, the coupling means 35 is configured to divide the main pump signal provided by the Brillouin Analyzer 34 to provide a first pump signal which has a higher power than the second pump signal.

The circulator circuit 31 is configured to prevent the propagation of the first pump signal from the first optical propagation path 23 to the second optical propagation path 26 and third propagation path 30, but to allow, the propagation of the probe signal, from the second optical propagation path 26 to the first optical propagation path 23. Thus, the optical circuit 31 will block the propagation of the first pump signal to ensure that the first pump signal does not propagate to beyond the first optical propagation path 23.

The optical circuit 31 is also configured to allow the propagation of the second pump signal from the third optical propagation path 30 to the second optical propagation path 26 and to prevent the propagation of the probe signal from second optical propagation path 26 to the third optical propagation path 30.

The optical circuit 31 controls the propagation direction of signals. The first pump signal does not propagate to beyond the first optical propagation path 23, as it cannot pass through the optical circuit 31 and therefore will not propagate into the second optical path 26; likewise spontaneous Brillouin Stokes and anti-Stokes waves which were generated by a probe signal as it propagates through the first optical propagation path 23, also will not propagate to the second optical propagation path 26. In contrast, as the second pump signal propagates from the third optical propagation path 30 to the second optical propagation path 26; the second pump signal therefore propagates through the optical circuit 31 and through the amplifier 32 so that the second pump signal is amplified before beginning propagation along the second optical propagation path 26. It should be noted that preferably the amplifier 32 may be, by default a single directional system; thus the first pump signal which propagates in the first optical propagation path 23, would not be amplified by the amplifier 32, even in the absence of the optical circuit 31.

In use the Brillouin Analyzer 34 provides a main pump signal which is received by the coupling means 35. Simultaneously, the Brillouin Analyzer 34 provides a probe signal which propagates, along the second optical propagation path 26.

Once the main pump signal is received by the coupling means 35 the coupling means 35 divides the main pump signal to provide a first pump signal which has a higher power than the second pump signal. The first pump signal propagates along the first optical propagation path 23 and a second pump signal which propagates along the third optical propagation path 30. The first and second pump signals propagate to the optical circuit 31. The optical delay line 39 will delay the propagation of the second pump signal along the third optical propagation path 30, thus ensuring that a backscattered signal resulting from the first pump signal and a backscattered signal resulting from the second pump signal when it propagates in the second optical propagation path 26, can be received at different times at the Brillouin Analyzer 34; thus both backscattered signals are not mixed thereby allowing easier analysis of the signal. The optical delay line 39 will also ensure that the first pump signal is received at the optical circuit 31 before the second pump signal.

The probe signal propagates along the second optical propagation path 26 and is received by the optical circuit 31. The optical circuit 31 will prevent the propagation of the probe signal from the second optical propagation path 26 to the third propagation path 30, but will allow the propagation of the probe signal from the second optical propagation path 26 to the first optical propagation path 23. Thus, the probe signal can cooperate only with the first pump signal, which propagates in the first optical propagation path 23, but not with the second pump signal which propagates in the third optical propagation path 30.

As the first pump signal propagates along the first optical propagation path 23, temperature and strain variations in the first pipe 21 will cause Brillouin scattering which creates a Brillouin backscattered signal. The probe signal which propagates along the first optical propagation path 23 will cooperate with the first pump signal which propagates along the first optical propagation path 23, to stimulate the Brillouin backscattered signal; thus providing the Brillouin backscattered signal with a higher signal to noise ratio. The Brillouin scattering properties of the Brillouin backscattered signal can be measured to determine strain and temperature variations within the first pump 21.

Additionally, spontaneous Brillouin Stokes and anti-Stokes waves, are generated in the first optical propagation path 23 by the probe signal while propagating through the first optical propagation path 23; the spontaneous Brillouin Stokes and anti-Stokes waves are a source of detrimental noise. As the probe signal is prevented from propagating along the third propagation path 30, spontaneous Brillouin Stokes and anti-Stokes waves which are generated as the probe signal propagates, will not be generated in the third propagation path 30. Thus, the second pump signal which propagates in the third propagation path 30 is not affected by noise created by spontaneous Brillouin Stokes and anti-Stokes waves.

Once the first pump signal has propagated along the first optical propagation path 23, the first pump signal will comprise noise due to the spontaneous Brillouin Stokes and anti-Stokes waves generated by the probe signal. The optical circuit 31 will prevent the propagation of the first pump signal from the first optical propagation path 23 to the second optical propagation path 26 and third propagation path 30. Thus, the optical circuit 31 will block the propagation of the noisy first pump signal to ensure that the first pump signal does not propagate to beyond the first optical propagation path 23, and in particular does not propagate into the second and third optical propagation paths 26,30.

Advantageously, preventing the propagation of the probe signal from the second optical propagation path 26 to the third optical propagation path 30 ensures, that the second pump signal is spectrally pure (i.e. is without stokes/anti-stokes components generated by counter propagating probe), and has less amount of noise, when received at the optical circuit 31. Furthermore, as the optical circuit 31 blocks the noisy first pump signal so that it cannot propagate from the first optical propagation path 23 to the second optical propagation path 26, but allows the second pump signal to propagate from the third propagation path 30 to the second optical propagation path 26, a spectrally pure pump signal propagates from the third optical propagation path 30 into the second optical propagation path 26. Thus, before the second pump signal begins to propagate along the second optical propagation path 26, the second pump signal is spectrally pure.

The spectrally pure, second pump signal, is amplified by the amplifier 32 before the second pump signal begins propagation along the second optical propagation path 26. The amplification of the second optical pump signal compensates for the fiber losses which occurred as the second pump signal propagated along the third optical propagation path 30. Preferably, the amplification of the second optical pump signal will be such that the second optical pump signal has at least the same power, or has greater power, than the first optical pump signal before first optical pump signal begins propagation along the first optical propagation path 23. The optical circuit 31 directs the now amplified, spectrally pure, second pump signal, to the second optical propagation path 26 and prevents the propagation of the noisy first pump signal and spontaneous Brillouin Stokes and anti-Stokes waves which were generated in the first optical propagation path 23, to the second optical propagation path 26. Thus, only the spectrally pure, amplified second pump signal propagates in the second optical propagation path 26; this enables a high quality sensing measurement of the temperature and strain in the second pipe 37.

In a similar manner to the first pump signal, as the second pump signal propagates along the second optical propagation path 26, temperature and strain variations in the second pipe 37 will effect Brillouin scattering within the second optical fiber 26; the Brillouin scattering creates a Brillouin backscattered signal. The probe signal which propagates along the second optical propagation path 26 will cooperate with the second pump signal which propagates along the second optical propagation path 26, to stimulate the Brillouin backscattered signal; thus providing the Brillouin backscattered signal with a higher signal to noise ratio. The Brillouin scattering properties of the Brillouin backscattered signal can be measured to determine strain and temperature variations within the second pipe 37. As the noisy first pump signal was blocked from propagating to the second optical propagation path 26, the Brillouin backscattered signal will be unaffected by noise generated in the first optical propagation path 23; thus there will be less noise present in the Brillouin backscattered signal which propagates in the second optical propagation path 26 thereby enabling a high quality sensing measurement of the temperature and strain in the second pipe 37.

Thus, two Brillouin backscattered signals are generated; a first Brillouin backscattered signal is generated in the first optical propagation path 23 and a second Brillouin backscattered signal is generated in the second optical propagation path 26. The Brillouin scattering properties of the first Brillouin backscattered signal can be measured to determine strain and temperature variations within the first pump 21. The Brillouin scattering properties of the second Brillouin backscattered signal can be measured to determine strain and temperature variations within the second pipe 37.

For each of the Brillouin backscattered signals, the frequency information of Brillouin backscattered light can be exploited to measure the local temperature or strain information along the optical fibres 24,26; and thus the local temperature or strain information of the pipes 21,37 with which the optical fibers 24,26 respectively cooperate.

Frequency domain analysis and time domain analysis can be carried out on each of the Brillouin backscattered signals. Time domain analysis can be used to determine one or more positions/locations along the pipes 21,37 and frequency domain analysis can be used to determine temperature and strain values at these one or more position/location.

In Frequency domain analysis the temperature/strain information is coded in the Brillouin frequency shift. Scanning the probe frequency with respect to the pump while monitoring the intensity of the backscattered signal allows to find the Brillouin gain peak, and thus the corresponding Brillouin shift, from which the temperature or the strain can be computed. This is achieved by using two optical sources, e.g. lasers, or a single optical source from which both the pump signal and the probe signal are created. In this case, an optical modulator (typically a telecommunication component) is used to scan the probe frequency in a controlled manner.

In time domain analysis, due to the pulsed nature of the pump, the pump/probe interaction takes place at different location along the fibre at different times. For any given location, the portion of probe signal which interacted with the pump arrives on a detector after a time delay equal to twice the travelling time from the fibre input to the specified location. Thus, monitoring the backscattered intensity with respect to time, while knowing the speed of light in the fibre, provides information on the position where the scattering took place.

It is advantageous to be able to control the amplification of the second pump signal, from a remote location. This is particularly the case for sub-sea applications, for example, if the sensor 20 is used to sense the properties of sub-sea pipes. Remote control of the amplification of the second pump signal allows a user to control the amplification of the second pump signal from land. Controlling the amplification of the second pump signal can be achieved by controlling the gain which is provided by an amplifier in the sensor; an amplifier which provides a higher gain will amplify the second pump signal more than an amplifier which provides a lower gain.

Figure 5:
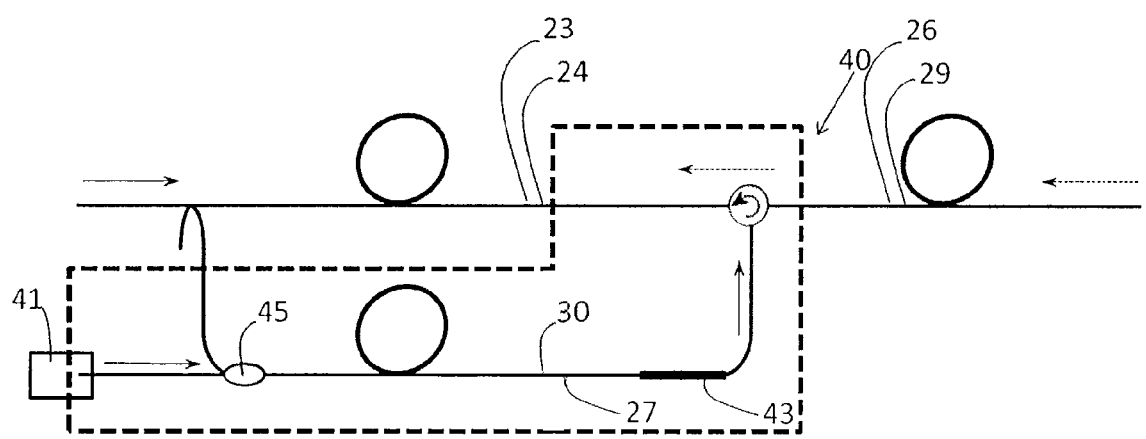
FIG. 5 illustrates a sensor according to a further possible embodiment of the present invention.

FIG. 5 provides a schematic diagram showing a sensor 40 according to a further embodiment of the present invention. The embodiment shown in FIG. 5 has many of the same features as the embodiment shown in FIG. 4 and like features are awarded the same reference numerals. In the particular embodiment shown in FIG. 5 there is provided an amplifying means which comprises an optical pump 41 which provides a control signal and an amplifier slave 43 whose gain is dependent on the control signal provided by the optical pump 41. There is further provided a coupler 45 which is operable to couple the control signal with the second pump signal which propagates along the third optical propagation path 30; thus, the second pump signal and control signal can simultaneously propagate along the third optical propagation path 30.

The amplifier slave 43 may be located sub-sea for example, and the optical pump 41 may be located on land, and the user may control the gain provided by the amplifier slave 43 by adjusting the control signal provided by the optical pump 41.

In this particular example, the optical pump 41 is a pump which provides a signal which has a wavelength of 1480 nm; the amplifier slave 43 is an erbium doped optical amplifier (EDFA) which can be operated using a remote optical pump source; and the coupler 45 is a WDM coupler. However, it should be understood that any other suitable optical pump 41, amplifier slave 43, and coupler 45 may be used.

Figure 6:
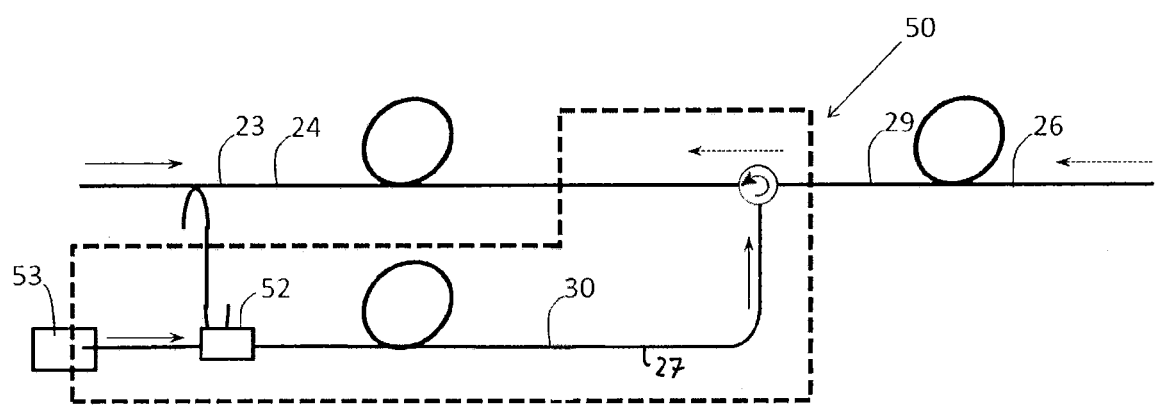
FIG. 6 illustrates a sensor according to a further possible embodiment of the present invention.

FIG. 6 shows a sensor 50 according to a further embodiment of the present invention. The embodiment shown in FIG. 6 has many of the same features as the embodiment shown in FIG. 4 and like features are awarded the same reference numerals. In the particular embodiment shown in FIG. 6, there is provided an amplifying means which comprises an optical parametric amplification (OPA) pump 53 which can provide an optical parametric amplification signal. There is further provided a coupler 52 which is operable to couple the optical parametric amplification signal with the second pump signal which propagates along the third optical propagation path 30; thus, the second pump signal and optical parametric amplification signal couple and simultaneously propagate along the third optical propagation path 30. The coupler 52 may take any suitable form.

The optical parametric amplification signal generates an optical parametric gain resonance with a programmable spectral bandwidth and net gain value while propagating through the third optical propagation path 30. When a central frequency of the optical parametric amplification signal is tuned such that the frequency of the second pump signal is in centre of the optical parametric gain resonance, then the second pump signal will be amplified by the optical parametric amplification signal as both signals propagate along the third optical propagation path 30.

Usually, the spatial distribution of the optical parametric gain resonance provided by the optical parametric amplification signal tends to grow exponentially along the third optical propagation path 30. Thus, the gradual exponential losses suffered by the second pump signal due to the fiber intrinsic loss, is compensated for by the gain provided by the optical parametric amplification signal. Effectively, therefore, the third optical propagation path 30 becomes transparent for the second pump signal.

Furthermore, the second pump signal can be strongly amplified by increasing the power of the optical parametric amplification signal; power of the optical parametric amplification signal can be increased to ensure that the second pump signal, which propagates in the third optical propagation path 30, is amplified to have a sufficient power before it begins propagation along the second optical propagation path 26. The second pump signal has sufficient power if it has enough power to propagate along the whole length of second optical propagation path 26, without the power in the second pump signal dropping below a predetermined power threshold level. Preferably, the amplification of the second optical pump signal will be such that the second optical pump signal has at least the same power, or has greater power, than the first optical pump signal before first optical pump signal begins propagation along the first optical propagation path 23.

Figure 7:
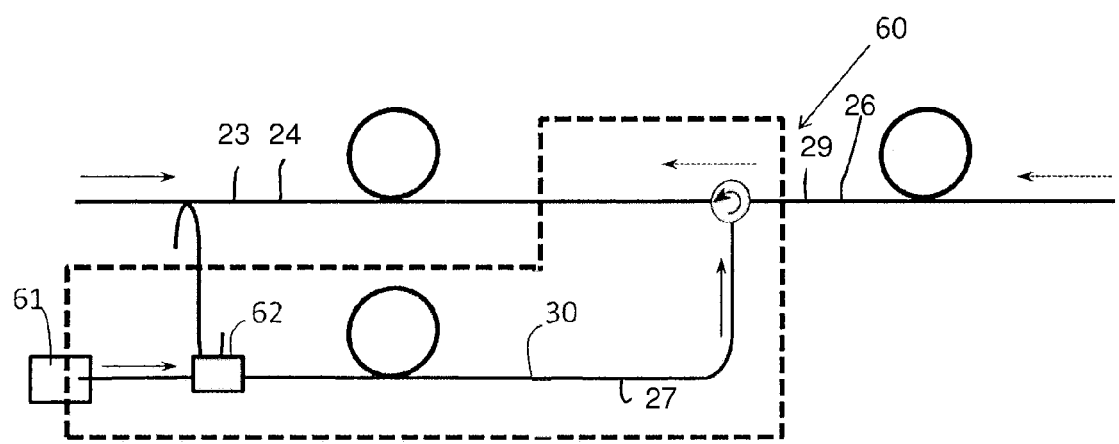
FIG. 7 illustrates a sensor according to a further possible embodiment of the present invention.

FIG. 7 shows a sensor 60 according to a further embodiment of the present invention. The embodiment shown in FIG. 7 has many of the same features as the embodiment shown in FIG. 4 and like features are awarded the same reference numerals. In this particular embodiment there is provided an amplifying means which comprises Raman amplification (RA) pump 61 which can provide a Raman amplification signal. There is further provided a coupler 62 which is operable to couple the Raman amplification signal with the second pump signal which propagates along the third optical propagation path 30; thus, the second pump signal and Raman amplification signal can simultaneously propagate along the third optical propagation path 30. The coupler 62 may take any suitable form.

The Raman amplification (RA) pump 61 should preferably be configured to provide an Raman gain which has a frequency which is equal to the frequency of the second pump signal; in this case the Raman gain will amplify the second pump signal as it propagate along the third optical propagation path 30.

Various modifications and variations to the described embodiments of the invention will be apparent to those skilled in the art without departing from the scope of the invention as defined in the appended claims. Although the invention has been described in connection with specific preferred embodiments, it should be understood that the invention as claimed should not be unduly limited to such specific embodiment.

What is claimed is:

1. A sensor, suitable for sensing one or more properties of one or more structures, the sensor comprising:
    a first optical propagation path which is configurable to cooperate with a structure whose properties are to be sensed;
    a second optical propagation path which is configurable to cooperate with a structure whose properties are to be sensed;
    a third optical propagation path;
    an amplifier for amplifying a signal which propagates in the third optical propagation path, so that the signal is amplified before it begins propagation along the second optical propagation path;
    a circulator configured to prevent the propagation of signals from the second optical propagation path to the third optical propagation path;
    a means to prevent the propagation of signals from the first optical propagation path to the second optical propagation path, wherein the means to prevent the propagation of signals from the first optical propagation path to the second optical propagation path is further configured to allow the propagation of signals, from the second optical propagation path to the first optical propagation path and from the third optical propagation path to the second optical propagation path, and
    an analyser configured to provide a first pump signal to the first optical propagation path and a second pump signal to the third optical propagation path,
    wherein a first end of the first optical propagation path is connected to said analyser, and a second opposite end of the first optical propagation path is connected to said circulator, and
    wherein a first end of the third optical propagation path is connected to said analyser, and a second opposite end of the third optical propagation path is connected to said circulator, such that:
    the second pump signal propagates from the first end of the third optical propagation path in a direction towards the second opposite end of the third optical propagation path; and
    the first pump signal propagates from the first end of the first optical propagation path towards the second opposite end of the first optical propagation path.

2. A sensor according to claim 1 wherein the means to prevent the propagation of signals from the second optical propagation path to the third optical propagation path comprises a circulator circuit.

3. A sensor according to claim 1 wherein the third optical propagation path is configurable to be arranged remote to the one or more structures so that a signal propagating in the third optical propagation path is unaffected by properties of the one or more structures.

4. A sensor according to claim 1, wherein the signal generator is further configured to provide a first pump signal to the first optical propagation path, a second pump signal to the third optical propagation path, and a probe signal to the second optical propagation path, so that one or more distributed sensing techniques may be carried out to determine properties of the one or more structures.

5. A sensor according to claim 4 wherein the first pump signal is configured to have a higher power than the second pump signal.

6. A sensor according to claim 1, further comprising a coupler configured to divide a main pump signal to provide the first pump signal and second pump signal.

7. A sensor according to claim 1 wherein, the third optical propagation path is configured such that the time for a signal to propagate along the length of the third optical propagation path is equal to, or greater than, the time for a signal to propagate along the length of the first optical propagation path.

8. A method of sensing properties of one or more structures, using a sensor according to claim 1, comprising the steps of:
    arranging the first optical propagation path in cooperation with a structure whose properties are to be sensed;
    arranging the second optical propagation path in cooperation with a structure whose properties are to be sensed;
    propagating a first pump signal along the first optical propagation path in a direction from the first end of the first optical propagation path towards the second opposite end of the first optical propagation path, and propagating a second pump signal along the third optical propagation path in a direction from the first end of the third optical propagation path towards the second opposite end of the third optical propagation path;
    amplifying the second pump signal only such that the second pump signal is amplified before the second pump signal propagate along the second propagation path;
    providing a probe signal which propagates along the second optical propagation path, and along said first optical propagation path in a direction from the second end of the first optical propagation path towards the first end of the first optical propagation path to stimulate Brillouin scattering in both the first pump signal which propagates in the first optical propagation path and in the second pump signal which propagates in the second optical propagation path;

preventing the propagation of the probe signal along the third optical propagation path; and using a backscattered signal which has resulted from the Brillouin scattering, to determine properties of the one or more structures.

9. The method according to claim 8 further comprising the step of, blocking the propagation of signals from the first optical propagation path to the second optical propagation path.

10. The method according to claim 8 further comprising the step of, delaying the propagation of the second pump signal in the third optical propagation path.

11. The method according to claim 8 further comprising the step of, dividing a main pump signal to provide the first and second pump signal.

12. The method according to claim 8 further comprising the step of, remotely controlling the amplification of the second pump signal.

13. The method according to claim 8 further comprising the step of, providing a control signal which controls the amplification provided by an amplifier which is operable to amplify a pump signal.

14. A sensor, suitable for sensing one or more properties of one or more structures, the sensor comprising:
   a first optical propagation path which is configurable to cooperate with a structure whose properties are to be sensed;
   a second optical propagation path which is configurable to cooperate with a structure whose properties are to be sensed;
   a third optical propagation path;
   a means for amplifying a signal which propagates in the third optical propagation path, so that the signal is amplified before it begins propagation along the second optical propagation path;
   a means to prevent the propagation of signals from the second optical propagation path to the third optical propagation path,
   a means for providing a first pump signal to the first optical propagation path and a second pump signal to the third optical propagation path, and
   a means for providing a probe signal to the second optical propagation path, so that one or more distributed sensing techniques may be carried out to determine properties of the one or more structures, wherein:
      a first end of the first optical propagation path is connected to the means for providing a pump signal to the first optical propagation path and a second opposite end of the first optical propagation path is connected to said means to prevent the propagation of signals from the second optical propagation path to the third optical propagation path, and
      a first end of the third optical propagation path is connected to the means for providing a second pump signal to the third optical propagation path and a second opposite end of the third optical propagation path is connected to said means to prevent the propagation of signals from the second optical propagation path to the third optical propagation path, such that:
   a pump signal provided in the third optical propagation path, by said means for providing a pump signal, to propagate from the first end of the third optical propagation path in a direction towards the second, opposite end of the third optical propagation path; and
   a pump signal provided in the first optical propagation path, by said means for providing a pump signal, to propagate from the first end of the first optical propagation path towards the second, opposite, end of the first optical propagation path, wherein the sensor further comprises, a means to prevent the propagation of signals from the first optical propagation path to the second optical propagation path; and
   wherein the means to prevent the propagation of signals from the first optical propagation path to the second optical propagation path, is further configured to allow the propagation of signals, from the second optical propagation path to the first optical propagation path and from the third optical propagation path to the second optical propagation path.

15. A method of sensing properties of one or more structures, using a sensor according to claim 14, comprising the steps of:
   arranging the first optical propagation path in cooperation with a structure whose properties are to be sensed;
   arranging the second optical propagation path cooperation a structure whose properties are to be sensed;
   propagating a first pump signal along the first optical propagation path in a direction from the first end of the first optical propagation path towards the second, opposite, end of the first optical propagation path, and propagating a second pump signal along the third optical propagation path in a direction from the first end of the third optical propagation path towards the second, opposite, end of the third optical propagation path;
   amplifying the second pump signal only such that the second pump signal is amplified before the second pump signal propagate along the second propagation path; providing a probe signal which propagates along the second optical propagation path, and along said first optical propagation path in a direction from the second end of the first optical propagation path towards the first end of the first optical propagation path, to stimulate Brillouin scattering in both the first pump signal which propagates in the first optical propagation path and in the second pump signal which propagates in the second optical propagation path;
   preventing the propagation of the probe signal along the third optical propagation path; and
   using a backscattered signal which has resulted from the Brillouin scattering, to determine properties of the one or more structures.

* * * * *